United States Patent [19]

Saito et al.

[11] Patent Number: 4,710,509

[45] Date of Patent: Dec. 1, 1987

[54] SUBSTITUTED PHENYLSULFONYLAZOLES

[75] Inventors: Junichi Saito, Mitaka; Tatsuo Tamura, Hamura; Yoshio Kurahashi, Hachioji; Shigeru Uzawa, Sagamihara; Noboru Matsumoto, Hachioji; Naoko Yamaguchi, Hino, all of Japan

[73] Assignee: Nihon Tokushu Noyaku Seizo K. K., Tokyo, Japan

[21] Appl. No.: 876,547

[22] Filed: Jun. 20, 1986

Related U.S. Application Data

[63] Continuation-in-part of Ser. No. 771,454, Aug. 30, 1985, abandoned.

[30] Foreign Application Priority Data

Sep. 3, 1984 [JP] Japan .................. 59-182579

[51] Int. Cl.⁴ .................. C07D 249/08; C07D 233/56; A01N 43/50; A01N 43/653
[52] U.S. Cl. .................. 514/384; 514/398; 548/262; 548/337
[58] Field of Search .............. 548/337, 262; 514/398, 514/384

[56] References Cited

U.S. PATENT DOCUMENTS 4,115,060  9/1978  Finley et al. .................. 548/337

FOREIGN PATENT DOCUMENTS 0044394  1/1982  European Pat. Off. .......... 548/337
64181    5/1979  Japan ............................. 548/337

Primary Examiner—Richard A. Schwartz
Assistant Examiner—Robert C. Whittenbaugh
Attorney, Agent, or Firm—Sprung Horn Kramer & Woods

[57] ABSTRACT

Novel substituted phenylsulfonylazoles of the formula (I)

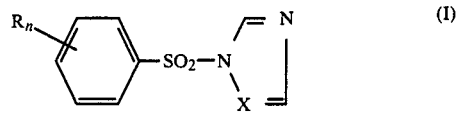

wherein
X represents N or a CH-group,
R represents halogen, lower alkyl, lower alkoxy, trifluoromethyl, nitrol, optionally halogeno-substituted phenyl or cycloalkyl, and
n represents 2 or 3, and furthermore, in case that R is not a methyl group, also represents 1, and the use of the new compounds as agricultural and horticultural fungicides.

11 Claims, No Drawings

SUBSTITUTED PHENYLSULFONYLAZOLES

This is a continuation-in-part of Application Ser. No. 771,454, filed Aug. 30, 1985, now abandoned.

The present invention relates to novel substituted phenylsulfonylazoles, to a process for their preparation and to their use as agricultural and horticultural fungicides.

It has already been disclosed that certain phenyl sulfonyl imidazole derivatives are useful as bleaching agents (Japanese Laid-Open Patent Application No. 64181/1979 resp. U.S. Pat. No. 4,115,060). Furthermore, according to the state of art 2-trichloromethyl-4-nitrophenyl-sulfonylimidazole posseses fungicidal activity (comp. EP-A No. 0 044 394).

Now, there have been found novel substituted phenylsulfonylazoles of the formula (I)

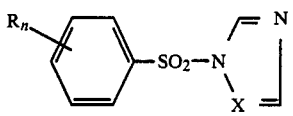

in which
X represents N or a CH group,
R represents halogen, lower alkyl, lower alkoxy, trifluoromethyl, nitro, optionally halogeno-substituted phenyl or cycloalkyl, and
represents 2 or 3, and furthermore, in case that R· is not a methyl group, also represents 1.

Substituted phenylsulfonylazoles of the formula (I) are obtained when substituted benzenesulfonyl halides of the formula (II)

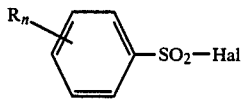

wherein R and n are as defined above, and Hal represents a halogen atom,
are reacted with azoles of the formula (III)

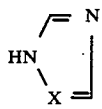

wherein X is as defined,
if appropriate, in the presence of acid acceptors and inert solvents.

The novel substituted phenylsulfonylazoles exhibit powerful agricultural and horticultural fungicidal properties.

Surprisingly, the substituted phenylsulfonylazoles according to the invention exhibit a substantially greater fungicidal action in agricultural and horticultural field than those known from the prior art and are not phytotoxic.

Among the substituted phenylsulfonylazoles of the formula (I) preferred compounds are those in which
X represents a CH group or nitrogen,
R represents chlorine, bromine, alkyl with 1 to 4 carbon atoms, alkoxy with 1 to 4 carbon atoms, nitro, phenyl and/or cycloalkyl with 5 to 6 carbon atoms, and
n represents 2 or 3, and furthermore, in case that R is not a methyl group, also represents 1.

Particularly preferred substituted phenylsulfonylazoles of the formula (I) are those in which
X represents a CH-group,
R represents chlorine, bromine, methyl, ethyl, nitro or phenyl, and
n represents 2 and furthermore, in case that R is not a methyl group, also represents 1.

Very particularly preferred are such compounds according to the instant invention where
X represents a CH group,
R represents methyl, nitro, bromine and chlorine, and
n represents the numerical value 2 and the two R-substituents are in 2,5-position.

Specifically, the following compounds may be mentioned:
1-(5-nitro-2-methyl-phenylsulfonyl)-imidazole,
1-(2,5-dimethyl-phenylsulfonyl)-imidazole,
1-(2-biphenylylsulfonyl)-imidazole,
1-(5-bromo-2-methyl-phenylsulfonyl)-imidazole.

The preparation of a compound of the general formula (I) may be illustrated as follows: If, for example, 5-nitro-2-methyl-phenylsulfonyl chloride and imidazole are used as starting materials, the course of the reaction can be represented by the following reaction equation:

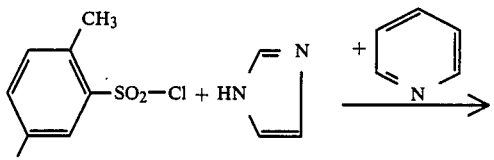

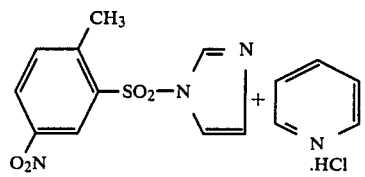

The formula (II) provides a general definition of the substituted benzenesulfonyl halides required as starting materials for the synthesis of the compounds according to the invention. In this formula R and n preferably have the meanings already given above. Hal preferably means chlorine.

The compounds of the formula (II) are already well-known (for details see for example Beilstein's Handbuch der organischen Chemie, main volume (Hauptwerk) 11, from page 34, and the corresponding chapters in the supplement volumes (Ergänzungswerke)).

As examples there may be mentioned:
2,5-dichlorobenzenesulfonyl chloride,
2-isopropylbenzenesulfonyl chloride,
2,5-xylenesulfonyl chloride,
5-bromo-2-toluenesulfonyl chloride,
5-chloro-2-toluenesulfonyl chloride,
2-phenylbenzenesulfonyl chloride,
5-chloro-2-methoxybenzenesulfonyl chloride,
5-nitro-2-toluenesulfonyl chloride, and
5-chloro-2-cyclohexylbenzenesulfonyl chloride.

The azole compounds of the general formula (III) which are likewise starting materials are imidazole and 1,2,4-triazole. The compounds are well-known.

The process for the production of the compounds of the formula (I) according to the instant invention may be carried out desirably in a solvent or diluent. For this purpose inert organic solvents and diluents can be used. Examples of such solvents or diluents include:

Aliphatic, alicyclic and aromatic hydrocarbons, which may optionally be chlorinated, such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The reaction in accordance with the invention may be carried out in the presence of an acid acceptor. Examples of acid acceptors are the hydroxides, carbonates, bicarbonates and alcoholates of alkali metals, tertiary amines such as triethylamine, diethylaniline and preferably pyridine.

The above process can be carried out over a wide temperature range. Generally, it can be carried out at a temperature between about −20° C. and the boiling point of the mixture, preferably between about 0° C. and about 100° C. Desirably, the reaction is carried out under normal (ambient) pressure, but it is also possible to operate under elevated or reduced pressure.

In this reaction, about 1 to 3 mols of the azole compound of formula (III) are employed per 1 mol of substituted benzenesulfonyl halide of the formula (II). The working-up of the reaction products can be effected in a customary and generally known manner.

The active substances according to the invention exhibit powerful fungicidal effects in the field of agriculture and horticulture. They can therefore be used as agricultural and horticultural fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which fall under generic names listed above may be mentioned as examples, but not by way of limitation: Botrytis species, such as, for example, *Botrytis cinerea;* Plasmopara species, such as, for example, *Plasmopara viticola;* Uromyces species, such as, for example, *Uromyces appendiculatus;* Sphaerotheca species, such as, for example, *Sphaerotheca fuliginea;* Venturia species, such as, for example *Venturia inaequalis;* Podosphaera species, such as, for example, *Podosphaera leucotricha;* Phytophthora species, such as, for example, *Phytophthora infestans;* Erysiphe species, such as, for example, *Erysiphe graminis;* Puccinia species, such as, for example, *Puccinia recondita;* Fusarium species, such as, for example, *Fusarium culmorum;* Ustilago species, such as, for example, *Ustilago nuda* or *Ustilago avenae;* Septoria species, such as, for example, *Septoria nodorum;* Tilletia species, such as, for example, *Tilletia caries;* Xanthomonas species, such as, for example, *Xanthomonas oryzae;* Pseudomonas species, such as, for example, *Pseudomonas lachrymans;* Pyricularia species, such as, for example, *Pyricularia oryzae,* Pellicularia species, such as, for example, *Pellicularia sasakii;* Pyrenophora species, such as for example, *Pyrenophora teres* (conidia form Drechslera, Syn. Helminthosporium); Cochliobolus species, such as, for example, *Cochliobolus sativus* (conidia form Drechslera, Syn. Helminthosporium); Cercospora species, such as, for example, *Cercospora canescens.*

In particular, the novel compounds exhibit a very outstanding controlling efficacy against late blight of tomato (*Phytophthora infestans*). Furthermore, they show a good activity against rice blast (*Pyricularia oryzae*), downy mildew on cucumbers and melons (*Pseudoperonospora cubensis*) and downy mildew on grapes (*Plasmopara viticola*).

As an agricultural and horticultural fungicide, the compounds of the formula (I) in accordance with this invention may be used directly upon dilution with water, or in various formulations obtained by methods generally practiced in the production of agricultural chemicals using agriculturally acceptable adjuvants. In actual use, these various formulations may be applied directly or after diluting them with water to the desired concentrations.

The agricultural acceptable adjuvants as referred to herein include, for example, diluents (solvents, extenders, carriers), surface-active agents (solubilizing agents, emulsifiers, dispersing agents, wetting agents), stabilizers, stickers, aerosol propellants and synergists.

Examples of the solvents are water; furthermore organic solvents, such as hydrocarbons, for example n-hexane, petroleum ether, petroleum fractions, for example paraffin waxes, kerosene, light oils, middle oils and heavy oils, benzene, toluene, and xylene, furthermore halogenated hydrocarbons such as methylene chloride, carbon tetrachloride, ethylene chloride, ethylene dibromide, chlorobenzene and chloroform, alcohols such as methanol, ethanol, propanol and ethylene glycol, ethers such as diethyl ether, ethylene oxide and dioxane, alcohol ethers such as ethylene glycol monomethyl ether, ketones such as acetone and isophorone, esters such as ethyl acetate and amyl acetate, amides such as dimethylformamide and dimethylacetamide and sulfoxides such as dimethyl sulfoxide.

Examples of the extenders or carriers include inorganic powders, for example sulfur, slaked lime, magnesium lime, gypsum, calcium carbonate, silica, perlite, pumice, calcite, diatomaceous earth, amorphous silica, alumina, zeolites, and clay minerals (such as pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfonic acid esters (such as sodium laurylsulfate), arylsulfonic acids (such as alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (for example laurylamine, stearyl trimethyl ammonium chloride and alkyl dimethylbenzyl ammonium chloride) and polyoxyethylene alkylamines; nonionic surface-active agents such as polyoxyethylene glycol ethers (for example polyoxyethylene alkylaryl ethers and the condensation products thereof), polyoxyethylene glycol esters (for example polyoxyethylene fatty acid esters), and polyhydric alcohol esters for examples polyoxyethylene sorbitan monolaurate); and amphoteric surface-active agents.

Examples of other adjuvants include stabilizers; stickers (such as agricultural soaps, casein lime, sodium alginate, polyvinyl alcohol, vinyl acetate-type adhesives and acrylic adhesives); aerosol propellants (such as trichlorofluoromethane, dichlorofluoromethane, 1,2,2-trichloro-1,1,2-trifluoroethane, chlorobenzene, and lower ethers); combustion controlling agents for fumigants (such as nitrites, zinc powder, and dicyandiamide); oxygen-yielding agents (such as chlorates); effect-prolonging agents; dispersion stabilizers (such as casein, tragacanth, carboxymethyl cellulose and polyvinyl alcohol); and synergists.

The compounds of this invention can be formulated into various forms by methods generally practiced in the production of agricultural chemicals. Illustrative of such forms are emulsifiable concentrates, oil preparations, wettable powders, soluble powders, suspensions, dusts, granules, pulverulent preparations, fumigants, tablets, aerosols, pastes and capsules.

The agricultural and horticultural fungicide of this invention may contain about 0.1 to about 95% by weight, preferably about 0.5 to about 90% by weight, of the aforesaid active ingredient.

In actual use, the suitable amount of the active compound in the aforesaid various formulations and ready-to-use preparations is generally about 0.0001 to about 20% by weight, preferably about 0.005 to about 10% by weight.

The content of the active ingredient can be properly varied depending upon the type of the formulation, the method, purpose, time and locus of its application, the state of occurrence of diseases.

If required, the compounds of this invention may be used in combination with other agricultural chemicals, for example insecticides, other fungicides, miticides, nematocides, antiviral agents, herbicides, plant growth regulators and attractants, such as organophosphate compounds, carbamate compounds, dithio (or thiol) carbamate compounds, organochlorine compounds, dinitro compounds, organosulfur or organometallic compounds, antibiotics, substituted diphenyl ether compounds, urea compounds, and triazine compounds, and/or fertilizers.

Various formulations and ready-to-use preparations containing the aforesaid active ingredient of the invention can be applied by various methods generally practiced in the field of agricultural chemical application, for example spraying (liquid spraying, misting, atomizing, dusting, granule scattering, water surface application, pouring, etc.); soil application (mixing, sprinkling, vaporing and pouring etc.); surface application (such as coating, banding, dust coating and covering); and dipping. It can also be used by the so-called ultralow volume spraying method. According to this method, the active ingredient may be used in an amount of almost 100%.

The rate of application per unit area can be properly chosen, and is, for example, about 0.03 to about 10 kg, preferably about 0.3 to about 6 kg, per hectare.

According to this invention, there can be provided an agricultural and horticultural fungicidal composition comprising the compound of general formula (I) as an active ingredient and a diluent (a solvent and/or an extender and/or a carrier) and/or a surface-active agent, and if further required, a stabilizer, a sticker and a synergist.

This invention also provides a method for controlling a crop disease, which comprises applying to a pathogen and/or the locus of its occurrence and/or the locus of occurrence of a crop disease, the compound of general formula (I) either singly or in admixture with a diluent (a solvent and/or an extender and/or a carrier) and/or surface-active agent and if further required, a stabilizer, a sticker and a synergist.

The following examples illustrate the present invention specifically. It should be noted however that the invention is not limited to them alone.

PREPARATION EXAMPLES

Example 1

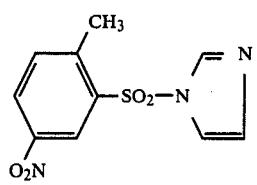

(Compound No. 1)

2.36 g of 5-nitro-2-methyl-phenylsulfonyl chloride (0.01 mol) and 1.36 g of imidazole (0.02 mol) were dissolved in 15 ml of pyridine, and the mixture was stirred at 50° C. for 3 hours to react. After the reaction, the reaction mixture was poured into water, and extracted with chloroform. The chloroform layer was washed with water and dehydrated. Evaporation of chloroform gave 1.70 g of 1-(5-nitro-2-methyl-phenylsulfonyl)-imidazole of the m.p. 119°–120° C.

Preparation of the starting product 50 ml of chlorosulfonic acid were added within 30 minute dropwise to a solution of 13.7 g of p-nitrotoluene in 50 ml of chloroform under ice cooling. After the addition, the mixture was refluxed for 6 hours. After refluxing, the reaction mixture was poured into ice water and extracted with chloroform. The chloroform layer was washed with water and dehydrated. Evaporation of chloroform gave 15.5 g of 5-nitro-2-methyl-phenylsulfonyl chloride of the m.p. 43°–44° C.

The following compounds of the general formula

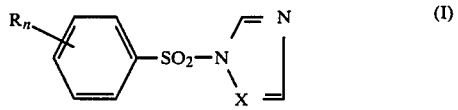

(I)

were obtained by the same method as described in Example 1:

| Compound No. | $R_n$ | x | Physical constant (mp. °C.) |
| --- | --- | --- | --- |
| 2 | 2-Cl | CH | 68–69 |
| 3 | 3-Cl | CH | 112–114 |

-continued

| Compound No. | $R_n$ | x | Physical constant (mp. °C.) |
|---|---|---|---|
| 4 | 2,3-$Cl_2$ | CH | 140–151 |
| 5 | 2,5-$Cl_2$ | CH | 99–100 |
| 6 | 2,4,5-$Cl_3$ | CH | 114–117 |
| 7 | 2-$C_3H_7$—iso | CH | 72–77 |
| 8 | 2,4-$(CH_3)_2$ | CH | 83–85 |
| 9 | 2,5-$(CH_3)_2$ | CH | 123–124 |
| 10 | 2,4,6-$(CH_3)_3$ | CH | 99–101 |
| 11 | 2-$CH_3$, 5-Br | CH | 112–116 |
| 12 | 2-$CH_3$, 5-Cl | CH | 88–190 |
| 13 | 2-$CH_3$, 4-F | CH | 84–87 |
| 14 | 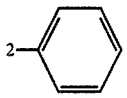 | CH | 111–113 |
| 15 | 4-Cl | N | 130–132 |
| 16 | 4-Br | N | 128–130 |
| 17 | 2,5-$Cl_2$ | N | 139–151 |
| 18 | 2,4,5-$Cl_3$ | N | 151–152 |
| 19 | 2-$OCH_3$, 5-Cl | N | 147–149 |
| 20 | 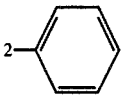 | N | 90–92 |
| 21 | 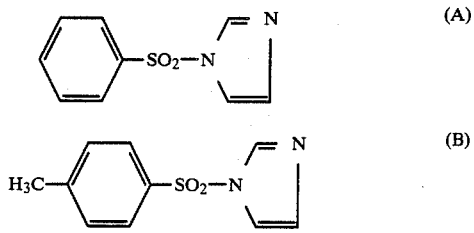 | CH | oil |
| 22 | 2-$C_2H_5$, 5-Br | CH | 102–103 |
| 23 | 2,6-$(CH_3)_2$, 3-$NO_2$ | CH | 79–81 |

USE EXAMPLES

The known comparison compounds are identified as follows:

(A) phenyl-$SO_2$-N(pyrrole)

(B) $H_3C$-phenyl-$SO_2$-N(pyrrole)

These compounds are described in the Japanese Laid Open Application No. 64181/1979 resp. in the U.S. Pat. No. 4,115,060.

EXAMPLE A

Late blight on tomato test (*Phytophora infestans*)

A test compound in the form of an emulsion prepared in accordance with formulation example (b) hereinafter was sprayed by a spray gun onto tomatoes (variety: Kurihara) cultivated in 9 cm unglazed pots. One day after the spraying, a suspension of spores of the above fungus was inoculated, and the pots were left to stand overnight in a constant temperature chamber kept at 22° C. and a humidity of more than 90%. Five days later, the degree of disease was rated as follows by the percentage of the area of lesions, and the control index was calculated:

| Degree of disease | Percentage (%) of the area of lesions |
|---|---|
| 0 | 0 |
| 0.5 | 2 or less |
| 1 | 3–5 |
| 2 | 6–15 |
| 3 | 16–30 |
| 4 | 31–50 |
| 5 | 51–or more |

Control index (%) = (Degree of disease of the non-treated area − Degree of disease of the treated area) / Degree of disease of the non-treated area × 100

As a result, all of the compounds (1) to (22) of this invention showed a control index of 100% when the concentration of the active ingredient was 250 ppm.

For control, the compounds (A) and (B) were tested in the same way as above. As a result, when the concentration of the active ingredient was 500 ppm, the compound (A) showed a control index of 40%, and the compound (B) a control index of 50%. At 250 ppm, both comparison compounds showed a control index of 0%.

EXAMPLE B

Rice blast test (*Pyricularia oryzae*)/foliar application

Each of the compounds (1) and (22) in the form of a wettable powder prepared in accordance with formulation example (a) hereinafter was sprayed onto rice plants in the 3- to 4-leaf stage. On the next day, a suspension of spores of the above fungus artificially cultivated was inoculated in the rice plants by spraying (twice) to induce infection. Seven days after the inoculation, the control indices (%) of the test compounds were determined in accordance with an ordinary rice blast control test. It was found that compounds Nos. 1 and 22 showed a control index of 100% when the concentration of the active compounds was 500 ppm.

FORMULATION EXAMPLES (a) Wettable powder:

Fifteen parts of compound No. 1 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and sprayed onto a pathogen and/or the locus of its occurrence and the locus of occurrence of a crop disease.

(b) Emulsifiable concentrate:

Thirty parts of compound No. 2 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto a pathogen and/or the locus of its occurrence and the locus of occurrence of a crop disease.

(c) Dust:

Two parts of compound No. 3 of the invention and 98 parts of powdery clay are pulverized and mixed to form a dust. It is scattered over a pathogen and/or the locus of its occurrence and the locus of occurrence of a crop disease.

(d) Dust:

Compound No. 34 of the invention (1.5 parts), 0.5 part of isopropyl hydrogen phosphate and 98 parts of powdery clay are pulverized and mixed to form a dust. It is scattered over a pathogen and/or the locus of its occurrence and the locus of occurrence of a crop disease.

(e) Granules:

Water (25 parts) is added to a mixture consisting of 10 parts of compound No. 3 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over a pathogen and/or the locus of its occurrence and the locus of occurrence of a crop disease.

We claim:

1. A substituted phenylsulfonylazole of the formula (I)

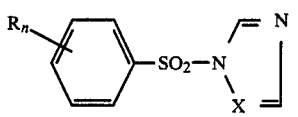

wherein
X is N or a CH-group,
R each independently is halogen, lower alkyl, lower alkoxy, trifluoromethyl, nitro, optionally halogeno-substituted phenyl or cycloalkyl, and
n is 2 or 3 and, if R is not a methyl group, may also be 1.

2. A compound according to claim 1, in which
R each independently is chlorine, bromine, alkyl with 1 to 4 carbon atoms, alkoxy with 1 to 4 carbon atoms, nitro, phenyl or cycloalkyl with 5 to 6 carbon atoms.

3. A compound according to claim 1, in which
X is a CH-group,
R each independently is chlorine, bromine, methyl, ethyl, nitro or phenyl.

4. A compound according to claim 1 of the formula

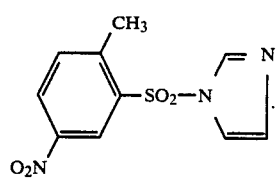

5. A compound according to claim 1 of the formula

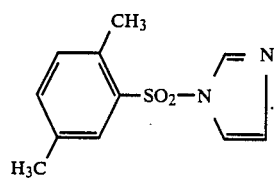

6. A compound according to claim 1 of the formula

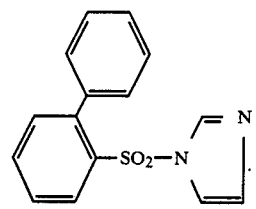

7. A compound according to claim 1 of the formula

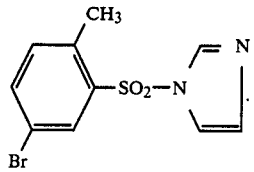

8. A compound according to claim 1 of the formula

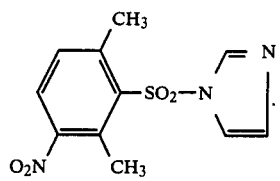

9. A fungicidal composition comprising a fungicidally effective amount of a compound according to claim 1 in admixture with a diluent.

10. A method of combating fungi, which comprises applying to such fungi or to a fungus habitat a fungicidally effective amount of a compound according to claim 1.

11. The method according to claim 10 wherein such compound is

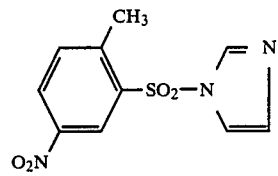

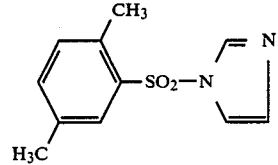

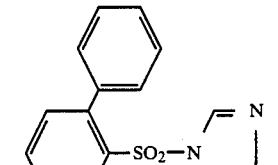

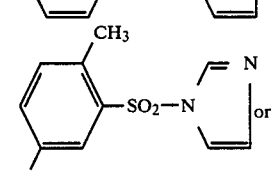

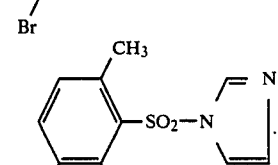

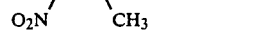

* * * * *